US00PP20090P3

(12) United States Plant Patent

Aréne et al.

(10) Patent No.: US PP20,090 P3

(45) Date of Patent: Jun. 9, 2009

(54) *HYDRANGEA* PLANT NAMED 'INOVALAUR'

(50) Latin Name: *Hydrangea hybrida/Hydrangea plant*
Varietal Denomination: Inovalaur

(75) Inventors: Laurence Aréne, Beaucouzé (FR); Alain Cadic, Beaucouzé (FR); Jean Paul Davasse, Beaucouzé (FR)

(73) Assignee: Agri Obtentions S.A., Guyancourt Cedex (FR)

( * ) Notice: Subject to any disclaimer, the term of this patent is extended or adjusted under 35 U.S.C. 154(b) by 0 days.

(21) Appl. No.: 12/155,825

(22) Filed: Jun. 10, 2008

(65) Prior Publication Data

US 2008/0307551 P1 Dec. 11, 2008

(51) Int. Cl.
*A01H 5/00* (2006.01)

(52) U.S. Cl. ..... Plt./250

(58) Field of Classification Search ..... Plt./250
See application file for complete search history.

*Primary Examiner*—Kent L. Bell
(74) *Attorney, Agent, or Firm*—Buchanan Ingersoll & Rooney PC

(57) ABSTRACT

A new and distinct *Hydrangea* plant is provided that was formed in the course of a planned breeding program. The plant is well-branched and displays a climbing growth habit. Attractive semi-persistent to persistent foliage is formed. Both large sterile and fertile flowers are exhibited. The plant can be grown to advantage where an attractive climbing ornamental plant is desired.

3 Drawing Sheets

Botanical/commercial classification: *Hydrangea hybrida/Hydrangea* Plant.
Varietal denomination: cv. Inovalaur.

SUMMARY OF THE INVENTION

The new *Hydrangea* plant was created during 1999 at Angers, France (Maine et Loire) by artificial pollination wherein two parents were crossed which previously had been studied in the hope that they would contribute the desired characteristics. The female parent (i.e., the seed parent) was an unnamed *Hydrangea anomala petiolaris* plant (non-patented in the United States). The male parent (i.e., the pollen parent) was an unnamed *Hydrangea semanii* plant (non-patented in the United States). *Hydrangea anomala petiolaris* is recognized to commonly display deciduous foliage, and *Hydrangea semanii* is recognized to form flowers having an umbel configuration. The parentage of the new hybrid *Hydrangea* plant can be summarized as follows:

*Hydrangea anomala petiolaris*×*Hydrangea semanii.*

The seeds resulting from the above pollination were sown and plants were obtained which were physically and biologically different from each other. Selective study resulted in the identification of a single plant of the new cultivar having the distinctive ornamental characteristics hereafter described.

It was found that the new *Hydrangea* cultivar of the present invention:

(a) displays an excellent branching character, (b) displays attractive semi-persistent to persistent foliage, (c) exhibits a propensity to climb, and (d) forms a combination of large sterile and fertile flowers.

The new cultivar well meets the needs of the horticultural industry. It can be grown to advantage in gardens and in the landscape where attractive climbing ornamentation is desired.

The new cultivar can be readily distinguished from each of its ancestors upon an observation of the propensity for foliage retention during the winter months and the appearance of the flowers.

The new cultivar has been asexually reproduced at Angers, France, by the rooting of cuttings. The characteristics of the new cultivar are firmly fixed and the new cultivar has been demonstrated to reproduce in a true to type manner in subsequence generations.

The new cultivar has been named 'Inovalaur'.

BRIEF DESCRIPTION OF THE PHOTOGRAPHS

The accompanying photographs show typical characteristics of the new cultivar during the summer when grown at Angers, France.

DETAILED DESCRIPTION

Figure 1:
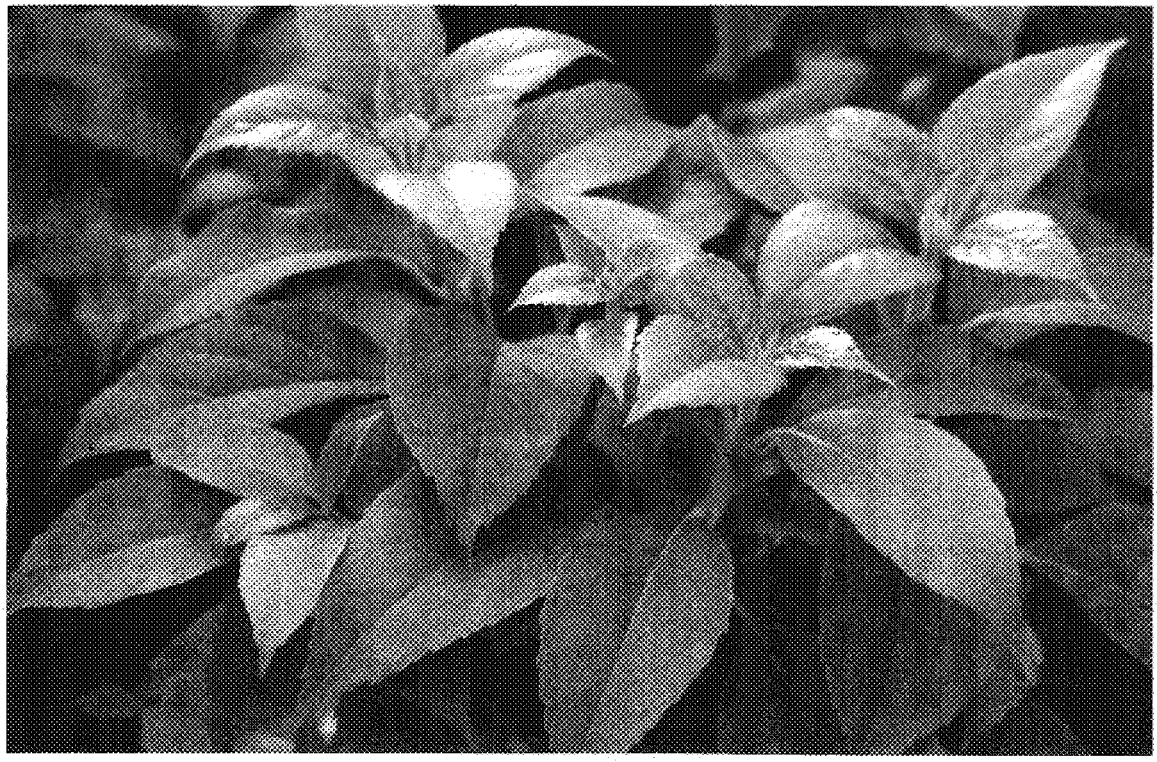
FIG. 1 shows the appearance of typical young and mature foliage.
Figure 2:
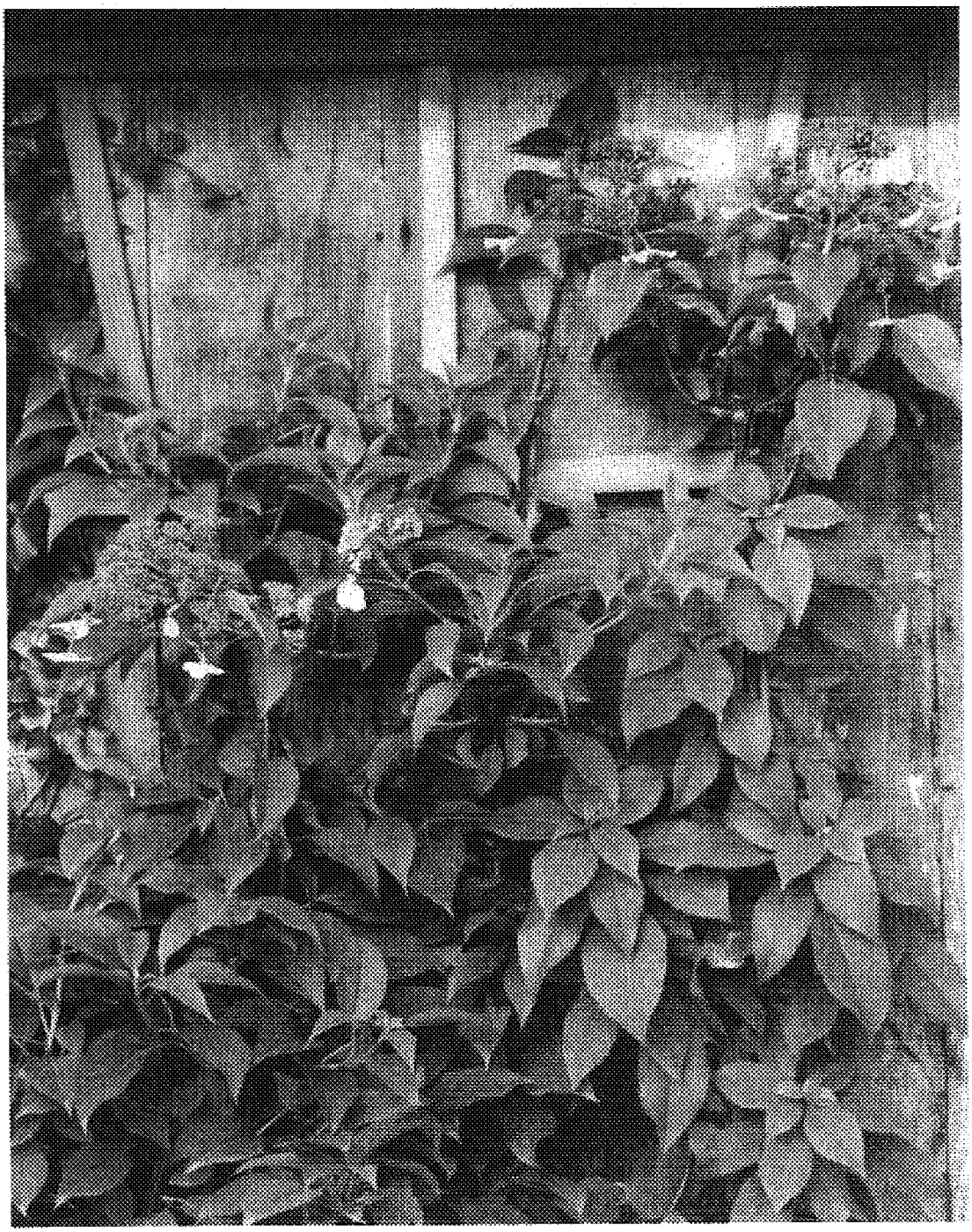
FIG. 2 shows the abundant branching and climbing character of the new cultivar.
Figure 3:
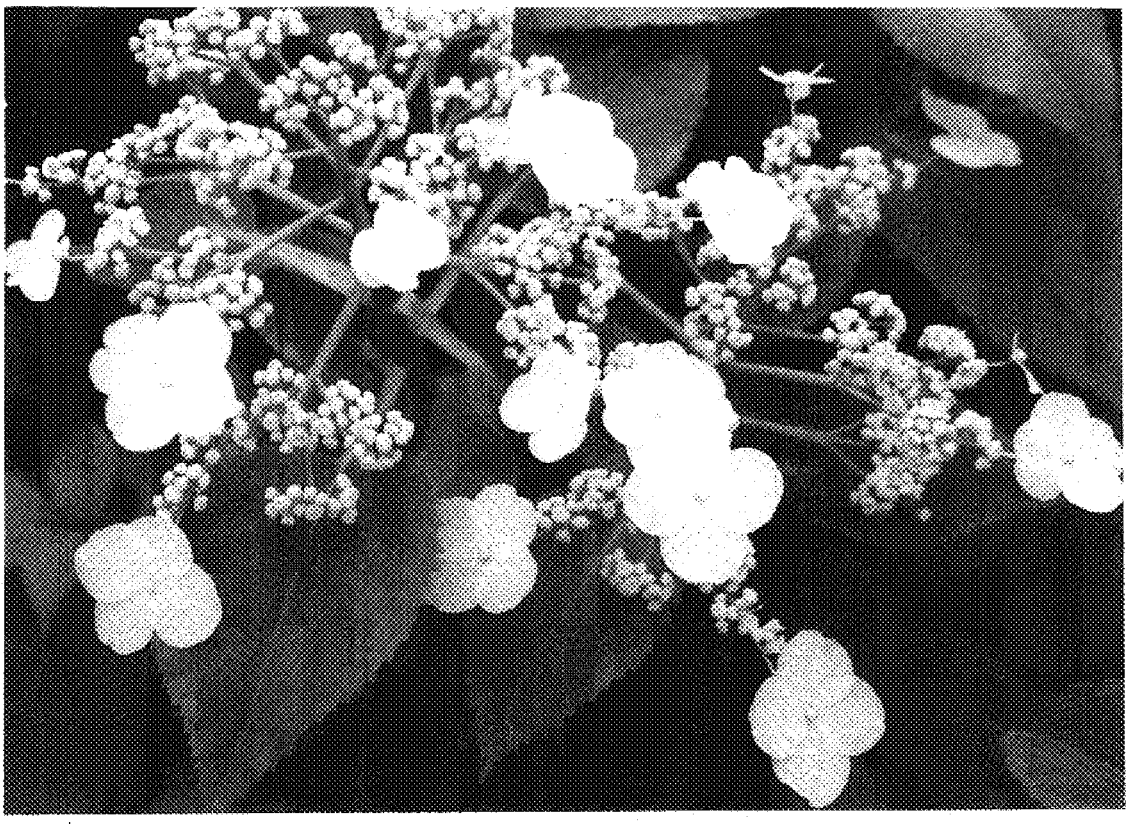
FIG. 3 shows a close view of the inflorescence in various stages of development with both fertile and infertile flowers being apparent.

The following description is based on the observation of three year-old plants of the new cultivar during May 2008, while being grown at Angers, France (Maine et Loire). Such plants had been asexually reproduced by the rooting of cuttings. Reference to the R.H.S. Colour Chart of the Royal Horticultural Society, London, England, is provided. Common color terms are accorded their customary dictionary significance.

Class: *Hydrangea.*

Origin: A product of a controlled breeding program involving the crossing of two species.

Plant

*Habit.*—Climbing.

*Height.*—Approximately 60 cm on average.

*Width.*—Approximately 45 cm on average.

Branches:

*Color.*—Yellow-Green Group 144A to 144C with some initial redness near Greyed-Orange Group 175A to 175B and Greyed-Orange Group 176A to 176B with some zones of Green Group 135A to 135B.

Foilage:

*General appearance.*—Rather dense.

*Configuration. —Ovate.*

*Margin.*—Serrated.

*Base.*—Substantially obtuse.

*Apex.*—Acuminate.

*Length.*—Approximately 12 to 13.5 cm on average.

*Width.*—Approximately 4.5 to 5.5 cm on average.

*Number of leaves per stem.*—Commonly approximately 10 to 12 on average.

*Color.*—Upper surface (new foliage): near Greyed-Orange Group 166C to 166D commonly with a slight border of Yellow-Green Group 154A to 154B. Under surface (new foliage): near Greyed-Orange Group 166C to 166D. Upper surface (mature foliage): near Green Group 137B to 137C. Under surface (mature foliage): near Yellow-Green Group 147B.

*Petiole.*—Length: commonly approximately 3 to 3.5 cm on average. Texture: sparse hairs of near White Group 155B on the upper surface, and very sparse hairs of near White Group 155B on the under surface. Color (upper surface): near Yellow-Green Group 146C to 146D commonly with some markings of Greyed-Orange Group 166B. Color (under surface): near Yellow-Green Group 144B to 144C.

Sterile inflorescence:

*Time.*—During May commonly for approximately 2 or 3 weeks at Angers, France (Maine et Loire).

*Form.*—Corymb.

*Number.*—Commonly approximately 9 to 12 on secondary branches.

*Buds.*—Color (upper surface): near Yellow-Green Group 150C to 150D. Color (under surface): near Yellow-Green Group 150C to 150D.

*Flowers.*—Shape: substantially flat. Diameter commonly approximately 2.4 to 2.6 cm on average. Petaloid sepal shape: generally regular and substantially globular commonly with a notch of approximately 1 mm at the tip. Petaloid sepal number commonly 4. Color (upper surface): near Yellow-Green Group 145A to 145C. Color (under surface): near Yellow-Green Group 145A to 145C. Fragrance: none. Lastingness: commonly approximately 2 to 3 weeks. Receptacle: commonly approximately 1.1 to 1.5 mm in length on average, and approximately 1 to 2 mm in width on average. Peduncle: commonly approximately 7.5 to 8.5 mm in length on average, approximately 0.6 to 0.8 mm in width on average, and near Yellow-Green Group 144B to 144C in coloration.

Fertile inflorescence:

*Time.*—During May commonly for approximately 2 or 3 weeks at Angers, France (Maine et Loire). Color: near Yellow-Green Group 145C. Receptacle: commonly approximately 1.5 to 2.25 mm in length on average, approximately 1.75 to 2.5 mm in width on average, and near Yellow-Green Group 144B to 144C in coloration. Peduncle: commonly approximately 1 to 2 mm in length on average, and approximately ≦0.5 mm in width, and near Yellow-Green Group 144B to 144C in coloration.

Development:

*Disease tolerance.*—Very good during observations to date with respect to common *Hydrangea* diseases.

*Tolerance to heat and cold.*—Grows well under the environmental conditions encountered at Angers, France (Maine et Loire).

*Hips.*—None observed.

Plants of the 'Inovalaur' cultivar have not been observed under all possible environmental conditions to date. Accordingly, it is possible that the phenotypic expression may vary somewhat with changes in light intensity and duration, cultural practices, and other environmental conditions.

We claim:

1. A new *Hydrangea* plant which exhibits the following characteristics:

(a) displays an excellent branching character, (b) displays attractive semi-persistent to persistent foliage, (c) exhibits a propensity to climb, and (d) forms a combination of large sterile and fertile flowers;

substantially as illustrated and described.

* * * * *